(12) United States Patent
Druliner et al.

(10) Patent No.: US 6,284,927 B1
(45) Date of Patent: Sep. 4, 2001

(54) HYDROPEROXIDE DECOMPOSITION PROCESS

(75) Inventors: Joe Douglas Druliner; Norman Herron, both of Newark; Stephen Paul Jordan, Wilmington, all of DE (US); Kostantinos Kourtakis, Swedesboro, NJ (US); Samuel Livingston Lane, Beaumont, TX (US); Leo Ernest Manzer; Bruce Edmund Smart, both of Wilmington, DE (US)

(73) Assignee: E. I. du Pont Nemours and Company, Wilmington, DE (US)

( * ) Notice: Subject to any disclaimer, the term of this patent is extended or adjusted under 35 U.S.C. 154(b) by 0 days.

(21) Appl. No.: 09/496,328

(22) Filed: Feb. 2, 2000

Related U.S. Application Data

(63) Continuation-in-part of application No. 09/254,612, filed as application No. PCT/US98/02926 on Feb. 10, 1998, now abandoned.
(60) Provisional application No. 60/037,564, filed on Feb. 11, 1997, and provisional application No. 60/045,165, filed on Apr. 30, 1997.

(51) Int. Cl.$^7$ ................................................. C07C 45/00
(52) U.S. Cl. ........................... 568/342; 568/376; 568/385
(58) Field of Search ................................... 568/322, 342, 568/376, 382, 385; 502/309, 305, 317, 316

(56) References Cited

U.S. PATENT DOCUMENTS

| | | | |
|---|---|---|---|
| 2,609,395 | 9/1952 | Dougherty, Jr. et al. | 260/586 |
| 2,675,407 | 4/1954 | Gallo et al. | 260/533 |
| 2,851,496 | 9/1958 | Cates, Jr. et al. | 260/586 |
| 2,854,487 | * 9/1958 | Quin . | |
| 3,093,686 | 6/1963 | Simon et al. | 260/586 |
| 3,530,185 | 9/1970 | Pugi | 260/586 |
| 3,598,869 | 8/1971 | Volpe et al. | 260/533 C |
| 3,917,708 | 11/1975 | Kuessner et al. | 260/586 R |
| 3,923,895 | 12/1975 | Costantini et al. | 260/586 P |
| 3,925,316 | 12/1975 | Brunie et al. | 260/586 R |
| 3,927,105 | 12/1975 | Brunie et al. | 260/586 P |
| 3,941,845 | 3/1976 | Voskuil et al. | 260/586 R |
| 3,957,876 | 5/1976 | Rapoport et al. | 260/586 P |
| 3,987,100 | 10/1976 | Barnette et al. | 260/586 R |
| 3,987,101 | 10/1976 | Wolters et al. | 260/586 R |
| 4,076,759 | 2/1978 | Field et al. | 260/621 |
| 4,326,084 | 4/1982 | Druliner et al. | 568/360 |
| 4,503,257 | 3/1985 | Druliner et al. | 568/342 |
| 4,581,126 | * 4/1986 | Day et al. . | |
| 4,783,557 | 11/1988 | Haneda et al. | 568/741 |
| 5,023,383 | 6/1991 | Inaba et al. | 568/815 |
| 5,364,988 | 11/1994 | Sanderson et al. | 568/909.8 |
| 5,399,794 | 3/1995 | Sanderson et al. | 568/909.8 |
| 5,401,889 | 3/1995 | Sanderson et al. | 568/909.8 |
| 5,414,141 | 5/1995 | Sanderson et al. | 568/578 |
| 5,414,163 | 5/1995 | Sanderson et al. | 568/909.8 |

FOREIGN PATENT DOCUMENTS

| | | | |
|---|---|---|---|
| 0 367 326 | 5/1990 | (EP) | C07C/45/33 |
| 0 453 021 | 10/1991 | (EP) | C07C/45/53 |
| 0 659 726 | 6/1995 | (EP) | C07C/45/53 |
| 0 676 238 A2 | 10/1995 | (EP) | B01J/31/18 |
| 1333129 | 10/1973 | (GB) | C07C/49/78 |
| WO 92/16487 | 10/1992 | (WO) | C07C/45/53 |
| WO 94/08932 | 4/1994 | (WO) | C07C/45/53 |
| WO 98/09931 | 3/1998 | (WO) | C07C/29/132 |

OTHER PUBLICATIONS

CA:123:209756 abs of Stud. Surf Sci Catal by Bernal et al 91(Preparation of Catalysts VI pp 461–70, 1995.*
CA:111:218376 abs of EP328715, Aug. 1989.*
CA:122:165056 abs of Hwahak Konghak by Kim et al 32(6) pp 844–52, 1994.*

* cited by examiner

*Primary Examiner*—Jean F. Vollano

(57) ABSTRACT

An improved process for decomposing alkyl or aromatic hydroperoxides to form a decomposition reaction mixture containing the corresponding alcohol and ketone. The improvement relates to decomposing the hydroperoxide by contacting the hydroperoxide with a catalytic amount of a heterogenous catalyst of Au, Ag, Cu or a sol-gel compound containing particular combinations of Fe, Ni, Cr, Co, Zr, Ta, Si, Mg, Nb, Al and Ti wherein certain of those metals have been combined with an oxide, such as an inorganic matrix of hydroxides or oxides, or combinations thereof. The catalysts may also optionally be supported on a suitable support member and used in the presence of an additional metal.

22 Claims, No Drawings

HYDROPEROXIDE DECOMPOSITION PROCESS

This application is a continuation-in-part of U.S. Ser. No. 09/254,612, filed on Aug. 25, 1999 which entered the United States as a 371 of PCT/US98/02926, filed on Feb. 10, 1998, now abandoned, which claims priority from Provisional Application No. 60/037,564, filed Feb. 11, 1997 and Provisional Application No. 60/045,165, filed on Apr. 30, 1997.

FIELD OF THE INVENTION

The invention generally relates to an improved catalytic process for decomposing alkyl or aromatic hydroperoxides to form a mixture containing the corresponding alcohol and ketone. In particular, the invention relates to decomposing a hydroperoxide by contacting it with a catalytic amount of a heterogenous catalyst of Au, Ag, Cu or a sol-gel compound containing particular combinations of Fe, Ni, Cr, Co, Zr, Ta, Si, Ti, Nb, Al and Mg, wherein certain of those metals have been combined with an oxide.

BACKGROUND OF THE INVENTION

Industrial processes for the production of mixtures of cyclohexanol and cyclohexanone from cyclohexane are currently of considerable commercial significance and are well described in the patent literature. In accordance with typical industrial practice, cyclohexane is oxidized to form a reaction mixture containing cyclohexyl hydroperoxide (CHHP). The resulting CHHP is decomposed, optionally in the presence of a catalyst, to form a reaction mixture containing cyclohexanol and cyclohexanone. In the industry, such a mixture is known as a K/A (ketone/alcohol) mixture, and can be readily oxidized to produce adipic acid, which is an important reactant in processes for preparing certain condensation polymers, notably polyamides. Due to the large volumes of adipic acid consumed in these and other processes, improvements in processes for producing adipic acid and its precursors can be used to provide beneficial cost advantages.

Druliner et al., U.S. Pat. No. 4,326,084, disclose an improved catalytic process for oxidizing cyclohexane to form a reaction mixture containing CHHP, and for subsequently decomposing the resulting CHHP to form a mixture containing K and A. The improvement involves the use of certain transition metal complexes of 1,3-bis(2-pyridylimino)isoindolines as catalysts for cyclohexane oxidation and CHHP decomposition. According to this patent, these catalysts demonstrate longer catalyst life, higher CHHP conversion to K and A, operability at lower temperatures (80–160° C.), and reduced formation of insoluble metal-containing solids, relative to results obtained with certain cobalt(II) fatty acid salts, e.g., cobalt 2-ethylhexanoate.

Druliner et al., U.S. Pat. No. 4,503,257, disclose another improved catalytic process for oxidizing cyclohexane to form a reaction mixture containing CHHP, and for subsequently decomposing the resulting CHHP to form a mixture containing K and A. This improvement involves the use of $Co_3O_4$, $MnO_2$, or $Fe_3O_4$ applied to a suitable solid support as catalysts for cyclohexane oxidation and CHHP decomposition at a temperature from about 80° C. to about 130° C., in the presence of molecular oxygen.

Sanderson et al., U.S. Pat. No. 5,414,163, disclose a process for preparing t-butyl alcohol from t-butyl hydroperoxide in the liquid phase over catalytically effective amounts of titania, zirconia, or mixtures thereof.

Sanderson et al., U.S. Pat. Nos. 5,414,141, 5,399,794 and 5,401,889, disclose a process for preparing t-butyl alcohol from t-butyl hydroperoxide in the liquid phase over catalytically effective amounts of palladium with gold as a dispersing agent supported on alumina.

Druliner et al., U.S. provisional application No. 60/025,368 filed Sep. 3, 1996 (now PCT US97/15332 filed Sep. 2, 1997), disclose decomposing a hydroperoxide by contacting it with a catalytic amount of a heterogenous catalyst of Zr, Nb, Hf and Ti hydroxides or oxides. Preferably, the catalyst is supported on $SiO_2$, $Al_2O_3$, carbon or $TiO_2$.

Further improvements and options are needed for hydroperoxide decomposition to K/A mixtures in order to overcome the deficiencies inherent in the prior art. Other objects and advantages of the present invention will become apparent to those skilled in the art upon reference to the detailed description which hereinafter follows.

SUMMARY OF THE INVENTION

In accordance with the present invention, an improved process is provided in which a hydroperoxide is decomposed to form a decomposition reaction mixture containing a corresponding alcohol and ketone. The improvement comprises decomposing hydroperoxide by contacting a hydroperoxide with a catalytic amount of a heterogenous catalyst selected from the group consisting of (1) Au (gold), (2) Ag (silver), (3) Cu (copper) and (4) sol-gel compounds comprised of (a) one or more members selected from a first group consisting of Cr, Co and Ti and (b) one or more members selected from a second group consisting of Fe, Ni, Zr, Ta, Nb, Si, Al, Mg and Ti, wherein the selected members of (b) are combined with an oxide and wherein members of the first group cannot be the same as members of the second group. Preferably, an inorganic matrix of hydroxides or oxides, or combinations thereof, is used as the oxide. Moreover, the catalysts are optionally supported on a suitable support member, such as $SiO_2$, $Al_2O_3$, carbon, zirconia, MgO or $TiO_2$. Zirconia and alumina are preferred supports.

Where the catalyst is gold, one or more metals selected from the group consisting of members of Periodic Group VIII may additionally be present. Preferably the metal is Pt or Pd. When one or more additional metals are present, the process may optionally be run in the presence of hydrogen gas.

DETAILED DESCRIPTION OF THE PREFERRED EMBODIMENTS

The present invention provides an improved process for conducting a hydroperoxide decomposition step in an industrial process in which an alkyl or aromatic compound is oxidized to form a mixture of the corresponding alcohol and ketone. In particular, cyclohexane can be oxidized to form a mixture containing cyclohexanol (A) and cyclohexanone (K). The industrial process involves two steps: first, cyclohexane is oxidized, forming a reaction mixture containing CHHP; second, CHHP is decomposed, forming a mixture containing K and A. As previously mentioned, processes for the oxidation of cyclohexane are well known in the literature and available to those skilled in the art.

Advantages of the present heterogenous catalytic process, relative to processes employing homogenous metal catalysts, such as metal salts or metal/ligand mixtures, include longer catalyst life, improved yields of useful products, and the absence of soluble metal compounds.

The improved process can also be used for the decomposition of other alkane or aromatic hydroperoxides, for example, t-butyl hydroperoxide, cyclododecylhydroperoxide and cumene hydroperoxide.

The CHHP decomposition process can be performed under a wide variety of conditions and in a wide variety of solvents, including cyclohexane itself. Since CHHP is typically produced industrially as a solution in cyclohexane from catalytic oxidation of cyclohexane, a convenient and preferred solvent for the decomposition process of the invention is cyclohexane. Such a mixture can be used as received from the first step of the cyclohexane oxidation process or after some of the constituents have been removed by known processes such as distillation or aqueous extraction to remove carboxylic acids and other impurities.

The preferred concentration of CHHP in the CHHP decomposition feed mixture can range from about 0.5% by weight to 100% (i.e., neat). In the industrially practiced route, the preferred range is from about 0.5% to about 3% by weight.

Suitable reaction temperatures for the process of the invention range from about 80° C. to about 170° C. Temperatures from about 110° C. to about 130° C. are typically preferred. Reaction pressures can preferably range from about 69 kPa to about 2760 kPa (10–400 psi) pressure, and pressures from about 276 kPa to about 1380 kPa (40–200 psi) are more preferred. Reaction time varies in inverse relation to reaction temperature, and typically ranges from about 2 to about 30 minutes.

As noted previously, the heterogenous catalysts of the invention include Au, Ag, Cu (including, but not limited to, Au, Ag and Cu sol-gel compounds) and certain non-Au/Ag/Cu sol-gel compounds, preferably applied to suitable solid supports. The inventive process may also be performed using Au, Ag or Cu in the presence of other metals (e.g., Pd). The metal to support percentage can vary from about 0.01 to about 50 percent by weight, and is preferably about 0.1 to about 10 wt. percent. Suitable, presently preferred supports include $SiO_2$ (silica), $Al_2O_3$ (alumina), C (carbon), $TiO_2$ (titania), MgO (magnesia) or $ZrO_2$ (zirconia). Zirconia and alumina are particularly preferred supports, and Au supported on alumina is a particularly preferred catalyst of the invention.

Some of the heterogenous catalysts of the invention can be obtained already prepared from manufacturers, or they can be prepared from suitable starting materials using methods known in the art. These methods can include sol-gel techniques as described in more detail below for preparing both Au/Ag/Cu sol-gel compounds and other non-Au/Ag/Cu sol-gel compounds. Supported gold catalysts can be prepared by any standard procedure known to give well-dispersed gold, such as evaporative techniques or coatings from colloidal dispersions.

In particular, ultra-fine particle sized gold is preferred. Such small particulate gold (often smaller than 10 nm) can be prepared according to Haruta, M., "Size-and Support-Dependency in the Catalysis of Gold", Catalysis Today 36 (1997) 153–166 and Tsubota et al., Preparation of Catalysts V, pp. 695–704 (1991). Such gold preparations produce samples that are purple-pink in color instead of the typical bronze color associated with gold and result in highly dispersed gold catalysts when placed on a suitable support member. These highly dispersed gold particles typically are from about 3 nm to about 15 nm in diameter.

The catalyst solid support, including $SiO_2$, $Al_2O_3$, carbon, MgO, zirconia, or $TiO_2$, can be amorphous or crystalline, or a mixture of amorphous and crystalline forms. Selection of an optimal average particle size for the catalyst supports will depend upon such process parameters as reactor residence time and desired reactor flow rates. Generally, the average particle size selected will vary from about 0.005 mm to about 5 mm. Catalysts having a surface area larger than 10 $m^2/g$ are preferred since increased surface area of the catalyst has a direct correlation with increased decomposition rates in batch experiments. Supports having much larger surface areas can also be employed, but inherent brittleness of high-surface area catalysts, and attendant problems in maintaining an acceptable particle size distribution, will establish a practical upper limit upon catalyst support surface area. A preferred support is alumina; more preferred is $\alpha$-alumina and $\gamma$-alumina.

Other catalysts useful in the present invention are comprised of certain metals (including metal ions) combined with an oxide, such as an inorganic matrix of hydroxides or oxides, or combinations thereof The metals include Fe, Ni, Cr, Co, Zr, Ta, Nb, Al, Si, Ti and Mg, present in combinations as set forth before. The mole percentage of metals in the matrix can vary, as can the number of different metals and their relative ratios. They also may have variable hydroxide content, which can depend on calcination temperature, if performed, and other parameters. The transition metals Co and Cr can be present as inorganic salts while Fe, Ni, Zr, Ta, Nb, Si, Al, Ti and Mg can be present as an oxide, a hydroxide, or combinations thereof. (Note that for simplification the corresponding anions are not shown for these cations in the formulae identified herein). Typical preparations involve sol-gel chemistry wherein the metals are co-hydrolyzed and/or entrapped within an inorganic matrix. Better dispersion and uniformity of the metal can be obtained compared to that normally attainable using more conventional synthetic methods. The inorganic matrix can optionally be supported on an appropriate support member, such as $SiO_2$, $Al_2O_3$, $ZrO_2$, carbon, MgO, or $TiO_2$. Preferred catalysts of this type are those containing Cr and/or Co.

A "sol-gel technique" is a process wherein a free flowing fluid solution, "sol", is first prepared by dissolving suitable precursor materials such as colloids, alkoxides or metal salts in a solvent. The "sol" is then dosed with a reagent to initiate reactive polymerization of the precursor. A typical example is tetraethoxyorthosilicate (TEOS) dissolved in ethanol. Water, with trace acid or base as catalyst to initiate hydrolysis, is added. As polymerization and crosslinking proceeds, the free flowing "sol" increases in viscosity and can eventually set to a rigid "gel". The "gel" consists of a crosslinked network of the desired material which encapsulates the original solvent within its open porous structure. The "gel" may then be dried, typically by either simple heating in a flow of dry air to produce a xerogel or the entrapped solvent may be removed by displacement with a supercritical fluid such as liquid $CO_2$ to produce an aerogel. These aerogels and xerogels may be optionally calcined at elevated temperatures (>200° C.) which results in products which typically have very porous structures and concomitantly high surface areas.

In practice of the invention, the catalysts can be contacted with CHHP by formulation into a catalyst bed, which is arranged to provide intimate contact between catalysts and reactants. Alternatively, catalysts can be slurried with reaction mixtures using techniques known in the art. The process of the invention is suitable for batch or for continuous CHHP decomposition processes. These processes can be performed under a wide variety of conditions.

Adding air or a mixture of air and inert gases to CHHP decomposition mixtures provides higher conversions of process reactants to K and A, since some cyclohexane is oxidized directly to K and A, in addition to K and A being formed by CHHP decomposition. This ancillary process is known as "cyclohexane participation", and is described in detail in Druliner et al., U.S. Pat. No. 4,326,084, the entire contents of which are incorporated by reference herein. Other gases may also be added or co-fed to the reaction mixture as needed. Inert gases such as nitrogen may also be added to the reaction alone or in combination with other gases.

The results of the CHHP decomposition reaction, such as the K/A ratio or conversion rate, can be adjusted by choice of catalyst support, gases added to the reaction mixture, or metals added to the heterogeneous catalysts of the invention.

Preferably, metals added to the heterogenous catalysts of the invention are for use as promoters, synergist additives, or co-catalysts are selected from Periodic Group VIII, hereby defined as Fe, Co, Ni, Ru, Rh, Pd, Os, Ir, and Pt. Most preferred is Pd and Pt.

One preferred gas that can be added to the reaction mixture is hydrogen. An advantage of the addition of hydrogen is that the K/A ratio can be varied according to need. The addition of hydrogen can also convert impurities or by-products of the reactions, such as benzene, to more desirable products. The hydrogen preferably is added to the process when the catalyst is gold with additional metals present.

The process of the present invention is further illustrated by the following non-limiting examples. In the examples, all temperatures are in degrees Celsius and all percentages are by weight unless otherwise indicated.

EXPERIMENTS

Experiment 1~1.4% Au on Carbon 5 g of 20–35 mesh (0.5–0.85 mm) charcoal carbon (EM Science, Cherry Hill, N.J.) was calcined in flowing helium (100 mL/min) at 400° C. for 1 hour. This material was then slurried into a solution of 0.1 g gold trichloride in 10 mL water containing 1 mL concentrated HCl. The slurry was stirred for 15 minutes at room temperature and then evaporated to dryness on a rotary evaporator. The recovered solid was calcined in flowing nitrogen (100 mL/min) at 400° C. for 1 hour, cooled and then stored in tightly capped vial for testing as a CHHP decomposition catalyst.

Experiment 2~1.4% Au on Silica 5 g of +8 mesh silica gel with surface area 300 $m^2$/g and pore volume 1 cc/g (Alfa Aesar, Ward Hill, Mass.) was calcined in flowing helium (100 mL/min) at 400° C. for 1 hour. This material was then slurried into a solution of 0.1 g gold trichloride in 10 mL water containing 1 mL concentrated HCl. The slurry was stirred for 15 minutes at room temperature and then evaporated to dryness on a rotary evaporator. The recovered solid was calcined in flowing nitrogen (100 mL/min) at 400° C. for 1 hour, cooled and then stored in tightly capped vial for testing as a CHHP decomposition catalyst.

Experiment 3~14% Au on Silica 5 g of <2 micron silica gel with surface area 450 $m^2$/g and pore volume 1.6 cc/g (Alfa Aesar, Ward Hill, Mass.) was calcined in flowing helium (100 mL/min) at 400° C. for 1 hour. This material was then slurried into a solution of 1.0 g gold trichloride in 10 mL water containing 1 mL concentrated HCl. The slurry was stirred for 15 minutes at room temperature and then evaporated to dryness on a rotary evaporator. The recovered solid was calcined in flowing nitrogen (100 mL/min) at 400° C. for 1 hour, cooled and then stored in tightly capped vial for testing as a CHHP decomposition catalyst.

Experiment 4—Plain Silica Control 5 g of +8 mesh silica gel with surface area 300 $m^2$/g and pore volume 1 cc/g (Alfa Aesar, Ward Hill, Mass.) was calcined in flowing helium (100 mL/min) at 400° C. for 1 hour. This material was then slurried into a solution of 10 mL water containing 1 mL concentrated HCl. The slurry was stirred for 15 minutes at room temperature and then evaporated to dryness on a rotary evaporator. The recovered solid was calcined in flowing nitrogen (100 mL/min) at 400° C. for 1 hour, cooled and then stored in tightly capped vial for testing as a CHHP decomposition catalyst.

Experiment 5~1.4% Au on α-Alumina 5 g of 6–12 mesh α-alumina spheres (Calsicat, Erie, Pa.) was slurried into a solution of 0.1 g gold trichloride in 10 mL water containing 1 mL concentrated HCl. The slurry was stirred for 15 minutes at room temperature and then evaporated to dryness on a rotary evaporator. The recovered solid was calcined in flowing nitrogen (100 mL/min) at 400° C. for 1 hour, cooled and then stored in tightly capped vial for testing as a CHHP decomposition catalyst.

Experiment 6~13% Ag on Silica 5 g of +8 mesh silica gel with surface area 300 $m^2$/g and pore volume 1 cc/g (Alfa Aesar, Ward Hill, Mass.) was calcined in flowing helium (100 mL/min) at 400° C. for 1 hour. This material was then slurried into a solution of 1.0 g silver nitrate in 10 mL water containing 1 mL concentrated $HNO_3$. The slurry was stirred for 15 minutes at room temperature and then evaporated to dryness on a rotary evaporator. The recovered solid was calcined in flowing nitrogen (100 mL/min) at 400° C. for 1 hour, cooled to 200° C. and calcined another 1 hour in flowing hydrogen (100 mL/min) and then stored in tightly capped vial for testing as a CHHP decomposition catalyst.

Experiment 7~4.5% Cu on Silica 5 g of +8 mesh silica gel with surface area 300 $m^2$/g and pore volume 1 cc/g (Alfa Aesar, Ward Hill, Mass.) was calcined in flowing helium (100 mL/min) at 400° C. for 1 hour. This material was then slurried into a solution of 1.0 g copper nitrate in 10 mL water containing 1 mL concentrated $HNO_3$. The slurry was stirred for 15 minutes at room temperature and then evaporated to dryness on a rotary evaporator. The recovered solid was calcined in flowing nitrogen (100 mL/min) at 400° C. for 1 hour, cooled to 200° C. and calcined another 1 hour in flowing hydrogen (100 mL/min) and then stored in tightly capped vial for testing as a CHHP decomposition catalyst.

Unlike Experiments 1–7, Experiments 8–13 were carried out according to the general gold deposition technique of Tsubota et al., Preparation of Catalysts V, pp. 695–704 (1991) to produce ultra-fine gold particles. These supported catalysts were purple/pink in color compared to the bronze/gold (higher loadings) or brown/grey (lower loadings) supported catalysts of Experiments 1–7.

Experiment 8~1% Au on MgO 10 g of powdered −200 mesh MgO (Alfa Aesar, Ward Hill, Mass.) was slurried into a solution of 0.2 g gold trichloride in 50 mL water containing 1 mL concentrated HCl. The pH of the slurry was adjusted to 9.6 with sodium carbonate solution and then 0.69 g sodium citrate was added. After stirring for 2 hours at room temperature the solid was recovered by filtration and washed well with distilled water. The recovered solid was calcined in flowing air (100 mL/min) at 250° C. for 5 hour, cooled and then stored in tightly capped vial for testing as a CHHP decomposition catalyst.

Experiment 9~1% Au on γ-Alumina 10 g of powdered −60 mesh γ-alumina (Alfa Aesar, Ward Hill, Mass.) was slurried into a solution of 0.2 g gold trichloride in 50 mL water containing 1 mL concentrated HCl. The pH of the slurry was adjusted to 9.6 with sodium carbonate solution and then 0.69 g sodium citrate was added. After stirring for 2 hours at room temperature the solid was recovered by filtration and washed well with distilled water. The recovered solid was calcined in flowing air (100 mL/min) at 250° C. for 5 hours, cooled and then stored in tightly capped vial for testing as a CHHP decomposition catalyst. The resulting catalyst was purple/pink in color and had a gold particle size of 8 nm as determined by x-ray diffraction (XRD).

Experiment 10~1% Au on Silica 10 g of silica +8 mesh granules (Alfa Aesar, Ward Hill, Mass.) was slurried into a solution of 0.2 g gold trichloride in 50 mL water containing 1 mL concentrated HCl. The pH of the slurry was adjusted to 9.6 with sodium carbonate solution and then 0.69 g sodium citrate was added. After stirring for 2 hours at room temperature the solid was recovered by filtration and washed well with distilled water. The recovered solid was calcined in flowing air (100 mL/min) at 250° C. for 5 hours, cooled and then stored in tightly capped vial for testing as a CHHP decomposition catalyst.

Experiment 11~1% Au on Titania 10 g of powdered −325 mesh titania (Alfa Aesar, Ward Hill, Mass.) was slurried into a solution of 0.2 g gold trichloride in 50 mL water containing 1 mL concentrated HCl. The pH of the slurry was adjusted to 7.0 with sodium carbonate solution and then 1.5 g sodium citrate was added. After stirring for 2 hours at room temperature the solid was recovered by filtration and washed well with distilled water. The recovered solid was calcined in flowing air (100 mL/min) at 400° C. for 5 hours, cooled and then stored in tightly capped vial for testing as a CHHP decomposition catalyst.

Experiment 12~1% Au on Zirconia 10 g −325 mesh zirconia (Calsicat #96F-88A, Erie, Pa.) was slurried into a solution of 0.2 g gold chloride in 50 mL water and 1 drop conc. HCl. The slurry was stirred gently as the pH was adjusted to 9.6 with 0.1 M sodium carbonate solution. The slurry was stirred gently while 0.69 g sodium citrate solid was slowly added and then stirred for 2 further hours. After filtering and washing well with distilled water, the solid was calcined in flowing air for 5 hours at 250° C.

Experiment 13~1% Au and 0.1% Pd on Alumina 10 g −60 mesh γ-alumina was slurried into a solution of 0.2 g gold and 0.02 g palladium tetraamine chloride in 50 mL water and one drop of conc. HCl. The slurry was stirred gently as the pH was adjusted to 9.6 with 0.1 M sodium carbonate solution. The slurry was again stirred gently while 0.69 g sodium citrate solid was slowly added and then stirred for 2 further hours. After filtering and washing well with distilled water, the solid was calcined in flowing air for 5 hours at 250° C.

Experiment 14

CrZrO $Cr_{0.05} (ZrO_{2-x}(OH)_{2x})_{0.95}$ 218 mL of ethanol (Quantum Chemical, Newark, N.J., dehydrated punctilious) was combined with 93.4 g of zirconium n-propoxide (70 wt† % in n-propanol, Alfa 22989, Ward Hill, Mass.) in an inert atmosphere $N_2$ drybox. 5.24 g of chromium (III) acetylacetonate (Aldrich, 20,223-2, Ward Hill Mass.) was dissolved in 218 mL of ethanol and was added to this solution. In a separate container, 218 mL of ethanol was mixed with 20.5 mL of water and 2.45 mL of glacial acetic acid (J. T. Baker, 6903–05, Phillipsburg, N.J.) and 1.91 mL of 70 wt % nitric acid (EM Sciences, Gibbstown N.J.).

The aqueous solution was added, in a dropwise fashion, to the zirconium alkoxide solution. The experiment was performed in a resin kettle under a blanket of flowing nitrogen during the addition of the aqueous solution. During hydrolysis, and prior to the observation of a gel point, some opaqueness and possible white particle formation was noted in the zirconium alkoxide solution. The opaque gel material was allowed to age at room temperature for at least 24 hours.

The material was dried at 120° C. in 1 atmosphere air prior to use. For some experiments, the material was pressed at 20,000 psi into small disks and granulated to sieve through −10, +20 mesh screens.

Experiment 15

CrTaO $Cr_{0.05} (TaO_{2-5-x} (OH)_{2x})_{0.95}$ 350 mL of ethanol (Quantum Chemical, Newark, N.J., dehydrated punctilious) was combined with 115.8 g of tantalum ethoxide $(Ta(OEt)_5$, Aldrich, 33, 91103, Milwaukee, Wis.) in an inert atmosphere $N_2$ drybox. 5.24 g of chromium (III) acetylacetonate (Aldrich, 20,223-2, Ward Hill Mass.) was dissolved in 350 mL ethanol added to the alkoxide solution. In a separate container, 350 mL of ethanol was mixed with 25.7 mL of water and 3.06 mL of glacial acetic acid (J. T. Baker, 6903-05, Phillipsburg, N.J.) and 2.39 mL of 70 wt % nitric acid (EM Sciences, Gibbstown N.J.).

The aqueous solution was added, in a dropwise fashion, to the tantalum alkoxide solution containing soluble chromium acetylacetonate. The material was contained in a resin kettle and was placed under a blanket of flowing nitrogen during this addition. Following hydrolysis, a clear, dark purple gel formed. A clear gel point was observed after approximately seven days at room temperature under flowing nitrogen.

The material was dried at 120° C. in 1 atmosphere air prior to use. For some experiments, the material was pressed at 20,000 psi into small disks and granulated to sieve through −10, +20 mesh screens.

Experiment 16

CrTiO $Cr_{0.2} (TiO_{2-x} (OH)_{2x})_{0.8}$ 13.85 mL of 60 volume % solution in ethanol containing titanium n-butoxide [Aldrich, 24-411-2) in ethanol was added to 50.08 mL of ethanol under an inert nitrogen atmosphere. 6.06 mL of a separate 1.5 molar (metals content) aqueous solution of 1.5 molar chromium hydroxide acetate [Aldrich, 31,810-8] was slowly added to the alcohol solution, with gentle swirling, to form the green colloidal gel. The material was dried at 120° C. in air prior to use.

Experiment 17

CoCrTiO $Co_{0.2}$ $Cr_{0.2}$ $(TiO_{2-x}$ $(OH)_{2x})$ 14.57 mL of a 60 volume % solution in ethanol containing titanium n-butoxide [Aldrich, 24-411-2] was added to 52.68 mL of ethanol. 8.50 mL of an aqueous 1.5 molar solution of chromium hydroxide acetate [Aldrich, 31,810-8] and 12.75 mL of a 1.0 M aqueous solution of cobalt chloride [Alfa, 12303], were added to the alkoxide solution. During the addition, the glass container was gently swirled under an inert nitrogen atmosphere. The gelled material was dried at 120° C. in air prior to use.

Experiment 18

TiSiO $Ti_{0.1}$ $Si_{0.9}$ $(O_{2-x}$ $(OH)_{2x})$ 1.915 mL of a tetraethylorthosilicate (Aldrich, 13,190-3) solution containing 60 volume % alkoxide in ethanol was added to 26.43 mL of titanium n-butoxide (Aldrich, 24,411-2) solution, also containing 60 volume % of the alkoxide in ethanol. 67.43 mL of ethanol was added to form a mixed alkoxide solution. The solution was kept under a nitrogen atmosphere.

A solution containing 3.712 mL of water mixed with 0.515 mL of glacial acetic acid (EM Sciences, X0409PS-1) was added to the alkoxide solution. During the addition of the aqueous components, the glass container was gently swirled under an inert nitrogen atmosphere. A gelatinous white gel formed almost immediately on addition and allowed to age at room temperature for at least 24 hours. The gelled material was dried at 120° C. in air prior to use.

Experiment 19

CoSiTiO $Co_{0.5}$ $Ti_{0.4}$ $Si_{0.1}$ $(O_{2-x}$ $(OH)_{2x})_{0.5}$ 3.86 mL of 60 volume % TEOS, 23.661 mL of 60 volume % titanium n-butoxide, and 16.45 mL of ethanol were used to form the alkoxide solution. To this solution, 3.74 mL of $H_2O$, 0.425 mL of glacial acetic acid, and 51.879 mL of a 1.0 M solution of cobalt (II) chloride (Alfa, 12303) in ethanol were added while gently swirling the glass container. A blanket of nitrogen gas was used throughout. A blue red gelatinous material was produced. After aging 24 hours in air, the material was dried at 120° C. prior to CHHP decomposition evaluations.

Experiment 20

AuMgCrTiO $Au_{0.00495}$ $Mg_{0.0099}$ $Cr_{0.00495}$ $(TiO_{2-x}$ $(OH)_{2x})_{0.98}$ 46.14 ml of ethanol (Quantum Chemical, 290, Newark, N.J., dehydrated punctilious) was combined with 20.214 ml of a 60 volume % solution in ethanol, containing titanium butoxide (Aldrich, 24,411-2), under an inert nitrogen atmosphere. 0.818 ml of an 0.219 M aqueous solution containing $AuCl_3$ (Aldrich, 33,404-9) (prepared using water and a 3:1 HCl:Au molar ratio of 37 wt % HCl, E.M. Sciences, Gibbstown, N.J.) was simultaneously added with 2.00 ml of 0.179 M aqueous magnesium citrate (Alfa, 39368), 0.119 ml of 1.5 M aqueous chromium hydroxide acetate, $Cr_3(OH)_2(CH_3COO)_7$ (Aldrich, 31,810-8), and 0.709 ml of glacial acetic acid, (J. T. Baker, 6903-05, Phillipsburg, N.J.).

The aqueous solutions were simultaneously added to the alkoxide solution. The container was gently swirled during this addition. A cloudy green/white gelatinous material was produced. After aging for at least 24 hours in air, the material was dried at 120° C. in a vacuum oven, and subsequently calcined to 250° C. in air for five hours, prior to CHHP decomposition evaluations.

Experiment 21

AuMgCrTiO $Au_{0.0227}$ $Mg_{0.0909}$ $Cr0.0227$ $(TiO_{2-x}(OH)_{2x})_{0.8636}$

The same procedure and reagents were used as described for Experiment 20, with the following differences:

3.216 ml of $AuCl_3$ solution 15.243 ml of titanium n-butoxide solution 15.749 ml of magnesium citrate solution 0.469 ml of chromium hydroxide acetate solution 34.789 ml of ethanol 0.535 ml of glacial acetic acid A cloudy green/white gel was produced, and was treated in the same manner as described for Experiment 20.

Experiment 22

AuMgCrZrO $Au_{0.0095}$ $Mg_{0.0476}$ $Cr_{0.0952}$ $(ZrO_{2-x}(OH)_{2-x})_{0.848}$ 1.836 ml of ethanol (Quantum Chemical, 290, Newark, N.J., dehydrated punctilious) was combined with 65.530 ml of a 0.558 M solution in ethanol containing zirconium n-propoxide (Alfa, 22989) under an inert nitrogen atmosphere. 1.827 ml of an 0.2248 M aqueous solution containing $AuCl_3$ (Aldrich, 33,404-9) was simultaneously added with 11.408 ml of 0.180 M magnesium citrate (Alfa, 39368), and 2.738 ml of 1.5 M aqueous chromium hydroxide acetate, $Cr_3(OH)_2(CH_3COO)_7$ (Aldrich, 31,810-8). The aqueous solutions were simultaneously added to the alkoxide solution. The container was gently swirled during this addition. A cloudy yellow/white gelatinous material was produced. After aging for at least 24 hours in air, the material was dried at 120° C. in a vacuum oven, and subsequently calcined to 250° C. in air for five hours, prior to CHHP decomposition evaluations.

Experiment 23

AuMgCrAlO $Au_{0.0095}$ $Mg_{0.0476}$ $Cr_{0.0952}$ $(AlO_{1.5-x}(OH)_{2x})_{0.8476}$ 69.574 ml of a 0.05 M solution, in ethanol, of aluminum isopropoxide (Aldrich, 22, 904-7) was added to the reactor container. In a second step, 0.525 ml of an 0.0744 M aqueous solution containing $AuCl_3$ (Aldrich, 33,404-9) was simultaneously added with 1.086 ml of 0.180 M aqueous magnesium citrate (Alfa, 39368), 0.361 ml of 1.5 M aqueous chromium hydroxide acetate, $Cr_3(OH)_2(CH_3COO)_7$ (Aldrich, 31, 810-8). The aqueous solutions were simultaneously added to the alkoxide solution. The container was gently swirled during this addition. A cloudy, red colored gel was produced. After aging for at least 24 hours in air, the material was dried at 120° C. in a vacuum oven, and subsequently calcined to 250° C. in air for five hours, prior to CHHP decomposition evaluations. This Experiment produced an aluminum based mixture of hydroxides and oxides.

Experiment 24

AuMgCrAlO $$Au_{0.0952} Mg_{0.0476} Cr_{0.190} (AlO_{1.5-x}(OH)_{2x})_{0.7524}$$

The same procedure was used as in Experiment 23, except for the volume changes listed below. A cloudy, red colored gel was produced.

0.592 ml of $AuCl_3$ solution 69.552 ml of the aluminum isopropoxide solution 1.223 ml of the magnesium citrate solution 0.587 ml of the chromium hydroxide acetate solution

Experiment 25

AuCrAlO $$Au_{0.01} Cr_{0.01} (AlO_{1.5-x}(OH)_{2x})_{0.98}$$

2500 ml of isopropanol (Em Sciences, PX1835-6) was combined with aluminum isopropoxide (Aldrich, 22,904-7) in an inert atmosphere $N_2$ drybox. The solid isopropoxide dissolved in the isopropanol over a 24 hour period. In a separate step, 0.3731 g of $AuCl_3$ (Aldrich, 33,404-9) was dissolved in 25 ml of ethanol (Quantum Chemical, Newark, N.J., dehydrated punctilious). A third solution containing 0.246 g of $Cr_3(OH)_2(CH_3COO)_7$ (chromium hydroxide acetate, Aldrich, 31,810-8) and 0.85 ml water (mixed with 8 ml of ethanol) was prepared.

The aluminum alkoxide solution was loaded into a resin kettle, and placed under a blanket of flowing nitrogen. The solution containing gold trichloride was transferred to a dropping funnel and added to the aluminum isopropoxide solution while stirring. The aqueous solution containing the chromium hydroxide acetate was then added to this mixed solution. Following hydrolysis, the solution was transparent. A gel point was observed after approximately twenty four hours under nitrogen. The final material was dark red, and was dried at 120° C. under vacuum. The xerogel was subsequently calcined at 250° C. in air for 5 hours prior to use.

Experiment 26

CrAlO $$Cr_{0.01} (AlO_{1.5-x}(OH)_{2x})_{0.98}$$

The same procedure was used as in Experiment 25, except that the gold salt was not added. 10.213 g of aluminum isopropoxide was combined with 1,000 ml of isopropyl alcohol. 0.1026 g of chromium hydroxide acetate was dissolved in 0.5 ml of $H_2O$, and then diluted with 3 ml of ethanol. A gel point was realized in 24 hours. The final xerogel was green in color, after drying under vacuum at 120° C. The material was calcined to 250° C. in air prior to use.

Experiment 27

AuMgCoTiO $$Au_{0.01} Mg_{0.05} Co_{0.2} (TiO_{2-x}(OH)_{2x})_{0.79}$$

Under an inert nitrogen atmosphere, 14.878 ml of 60 volume % in ethanol, containing titanium n-butoxide (Aldrich, 24,411-3) was added to a reaction container. Separate solutions containing 5.013 ml of 0.0659 M $AuCl_3$ solution (prepared by dissolving $AuCl_3$ (Aldrich, 33,440-9) in ethanol), 33.033 ml of ethanolic 0.2 M $CoCl_2$ solution (prepared by dissolving $CoCl_2.6H_2O$ Fisher, C-371 in ethanol) and 9.176 ml of 0.180M magnesium citrate solution (prepared by dissolving magnesium citrate pentahydrate in water) were prepared.

The three solutions were simultaneously added to the alkoxide solution. The container was gently swirled during this addition. A purple solution formed; a gel point could be realized in 24 hours. After drying under vacuum at 120° C., a purple xerogel formed. The material was calcined in air for 250° C. for 5 hrs prior to use.

Experiment 28

CoCrZrO $$Co_{0.1} CrO_{0.3} (ZrO_{2-x}(OH)_{2x})_{0.6}$$

5.1935 g of cobalt chloride ($CoCl_2$, Alfa, 12303, anhydrous), 24.1328 g of chromium hydroxide acetate ($Cr_3(OH)_2(CH_3COO)_7$, Aldrich, 31,910-8) was dissolved in 40 ml of $H_2O$ and 183.51 ml of ethanol (dehydrated, punctilious). In an inert atmosphere drybox, 78.6192 g of zirconium n-propoxide (Alfa, 22989) was combined with 183.51 ml of ethanol and placed in a resin kettle under flowing nitrogen. The aqueous solutions containing the cobalt chloride and chromium hydroxide acetate were slowly added to the zirconium alkoxide solution, with stirring. A cloudy, viscous gel formed almost immediately upon hydrolysis. The material was dried under vacuum at 120° C., as described previously.

Experiment 29

CrAlO $$Cr_{0.1} (AlO_{1.5-x}(OH)_{2x})_{0.9}$$

Under an inert nitrogen atmosphere, 25.966 ml an aluminum oxide sol (Nyacol, Al-20, 20 wt % $Al_2O_3$ in water) was added to a reaction container along with 7.97 ml of 1.689M aqueous chromium hydroxide acetate solution (Aldrich, 31,810-8). A dark black gel formed almost immediately (within minutes). The material was dried under vacuum, as described above, prior to use.

Experiment 30

CoNbTiO $$Co_{0.3} (NbO_{1.5-x}(OH)_{2x})_{0.01}(TiO_{2-x}(OH)_{2x})_{0.69}$$

Under an inert nitrogen atmosphere, 34.092 ml of anhydrous ethanol was added to 18.182 ml of a 60 volume % solution, in ethanol, containing titanium n-butoxide (Aldrich, 24,411-3) along with 1.52 ml of 0.304 M ethanolic solution of niobium ethoxide prepared by reacting $NbCl_5$ with ethanol (Johnson-Matthey, 11548). Separate solutions containing 13.866 ml of 1.0 M ethanolic $CoCl_2$ solution (prepared by dissolving $CoCl_2 \cdot 6H_2O$, Alfa, 36554) and 2.339 ml $H_2O$ were prepared.

The two solutions were simultaneously added to the alkoxide solution. The container was gently swirled during this addition. A blue solution formed; a gel point could be realized in 24 hours. After drying under vacuum at 120° C., a blue xerogel formed.

Experiment 31

AuCrTiO $$Au_{0.01} Cr_{0.2} (TiO_{2-x}(OH)_{2x})_{0.79}$$

Under an inert nitrogen atmosphere, 53.128 ml ethanol (punctilious) was added to 33.235 ml of 60 volume % solution, in ethanol, containing titanium n-butoxide (Aldrich, 24,411-3). Separate solutions containing 22.726 ml of 0.03247 M $AuCl_3$ solution (prepared by dissolving $AuCl_3$ (Aldrich, 33,440-9) in ethanol), 9.839 ml of aqueous 1.5 M chromium hydroxide acetate solution (prepared by dissolving $Cr_3(OH)_2(CH_3COO)_7$ (Aldrich, 31,810-8) in water)) were prepared.

The two solutions were simultaneously added to the alkoxide solution. The container was gently swirled during this addition. A dark green/purple solution formed; a gel point could be realized in 24 hours. After drying under vacuum at 120° C., a dark-green purple xerogel formed. The material was calcined in air for 250° C. for 5 hrs prior to use.

Experiment 32

AuAlO $$Au_{0.01} (AlO_{1.5-x}(OH)_{2x})_{0.98}$$

The same procedure as that of Experiment 25 was used, except that the chromium salt was not added. 10.213 g of aluminum isopropoxide was combined with 1,000 ml of isopropyl alcohol; 0.1548 g of $AuCl_3$ was dissolved in ethanol. A gel point was realized in 24 hours. The final xerogel was dark red/purple in color, after drying under vacuum at 120° C. The material was calcined to 250° C. prior to use.

Experiment 33

AuCrAlO $$Au_{0.0125} Cr_{0.1} [AlO_{1.5-2x}(OH)_{2x}]_{0.8875}$$

10.706 ml of aqueous $Al_2O_3$ colloid (Nyacol, Al-20, 20 wt % $Al_2O_3$) was simultaneously added with 23.462 ml of 0.03 M aqueous $AuCl_3$ solution (prepared by dissolving $AuCl_3$ (Aldrich 25-559-9) in water) and 3.334 ml of aqueous 1.6891 M chromium hydroxide acetate solution (1/3 $Cr_3$(OH)$_2$(CH$_3$COO)$_7$, Aldrich, 31-810-8). In a second step, 2.499 ml of 0.1 M HCl was added to further destabilize the colloid and form the aquagel. The container was gently swirled during the addition. A gel point was realized quickly. A dark brown formed. A xerogel formed after drying under vacuum at 120° C.

Experiment 34

NiCrAlO $$Ni_{0.1} Cr_{0.3} [AlO_{1.5-x} (OH)_{2x}]_{0.6}$$

15.824 ml of colloidal $Al_2O_3$ (Nyacol products, Al-20, 20% wt $Al_2O_3$) was added to a 150 ml container with gentle swirling. 12.311 ml of 1.0 M of aqueous solution of $Ni(NO_3)_2 \cdot 6H_2O$ was subsequently added along with 21.86 ml of 1.689M aqueous chromium hydroxide acetate (1/3 [$Cr_3$(OH)$_2$ (ac)$_7$], Aldrich 31810-8) were added and partially destabilized to alumina colloid. A dark red gelatinous material formed, and was dried at 120° C. for 5 hours prior to use to produce the xerogel powder.

Experiment 35

CoFeAlO $$Co_{0.1} Fe_{0.1} AlO_{1.5-x} (OH)_{2x}]_{0.8}$$

23.073 ml of colloidal $Al_2O_3$ (Nyacol products, Al-20, 20 wt 5 $Al_2O_3$) was added to a 150 ml container with gentle swirling. 13.463 ml of 1.0 M $CoCl_2 \cdot 6H_2O$ was subsequently added along with 13.463 ml of 1.0M aqueous solution $Fe(NO_3)_3 \cdot 6H_2O$ [Aldrich, 20,792-6)]. Following the addition of the metal salts, the aluminum oxide colloid de-stabilized to produce an aquagel which was dark brown in color. It was aged at least for 24 hours prior to drying under vacuum at 120° C. for five hours to produce the final xerogel catalyst.

Experiment 36

NiCrTiO $$Ni_{0.1} Cr_{0.3} (TiO_2)_{0.6}$$

6.043 ml of $TiO_2$ aqueous slurry (15.722 M, E. I. duPont de Nemours, Wilmington, Del.) was added to the 150 ml container with stirring. In a subsequent step, 15.834 ml 1.0 M of aqueous solution of $Ni(NO_3)_2 \cdot 6H_2O$ and 28.123 ml of 1.689M aqueous chromium hydroxide acetate (1/3 [$Cr_3$ (OH)$_2$ (ac)$_7$], Aldrich 31810-8) were added with gentle swirling. A gelatinous slurry formed was blue-grey in color. The material was dried at 120° C. for 5 hours under vacuum prior to use.

Experiment 37

FeNiCoTiO $$Fe_{0.1} Ni_{0.1} Co_{0.1} (TiO_2)_{0.7}$$

6.462 ml of $TiO_2$ aqueous slurry (15.722 M, E. I. du Pont de Nemours, Wilmington, Del.) was added to the 150 ml container with gentle stirring. In a subsequent step, 14.513 ml of 1.0 M of aqueous solution of $Ni(NO_3)_2 \cdot 6H_2O$, 14.513 ml of 1.0 M $CoCl_2 \cdot 6H_2O$, 14.513 ml of aqueous 1.0M aqueous solution $Fe(NO_3)_3 \cdot 6H_2O$ [Aldrich, 20,792-6)] were added. A yellow gelatinous slurry formed, which was subsequently dried at 120° C. for 5 hours under vacuum prior to use.

EXAMPLES

Examples 1–46 were run in batch reactor mode, in stirred 3.5 mL glass vials, sealed with septa and plastic caps. Vials were inserted into a block aluminum heater/stirrer apparatus that holds up to 8 vials. Stirring was done using TeflonO-coated stir bars. Each vial was first charged with 1.5 mL of n-octane or undecane solvent, approximately 0.005 or 0.01 g of a given crushed catalyst, a stir bar and the vial was sealed. Vials were stirred and heated approximately 10 minutes to assure that the desired reaction temperature of 125° C. had been attained. Next, at the start of each example, 30 pL of a stock solution of CHHP and TCB(1,2,4- trichlorobenzene) or CB (chlorobenzene), GC (gas chromatograph) internal standard, were injected. Stock solutions consisted of mixtures of about 20 wt % TCB or CB in CHHP. The CHHP source contained up to 2.0 wt % of combined cyclohexanol and cyclohexanone. Vials were removed from the aluminum heater/stirrer after a 0.5 to 10 minute period and were allowed to cool to ambient temperature.

In Examples 1–10 (Table I) vials were analyzed directly for the amount of CHHP remaining, using a 15 m DB-17 capillary column with a 0.32 mm internal diameter. The liquid phase of the column was comprised of (50 wt % phenyl) methyl polysiloxane. The column was obtained from J. and W. Scientific, Folsum, Calif.

GC analyses for the amounts of CHHP in each solution were calculated using the equation:

wt. % CHHP=(area % CHHP/area % TCB)×wt. % TCB×R.F.$_{CHHP}$

R.F.$_{CHHP}$ (GC response factor for CHHP) was determined from calibration solutions containing known amounts of CHHP and TCB, and was calculated from the equation:

$$R.F._{CHHP} = \frac{\text{wt. \% } CHHP/\text{area \% } CHHP}{\text{wt. \% } TCB/\text{area \% } TCB}$$

% CHHP Decomp.=100×[1−(area % CHHP/area % TCB)final/(area % CHHP/area % TCB initial]

In Examples 1–10 (Table I) the initial concentrations of CHHP in each vial were approximately 2.2 wt %. The GC wt % CHHP$_{initial}$ and CHHP$_{final}$ numbers are only approximate because the amount of TCB per g solution ratios used in GC calculations were arbitrarily all made equal to 0.25 mg TCB/g solution. Since an unheated sample of 1.5 mL n-octane and 30 μL CHHP/TCB solution was analyzed with each set of CHHP decomposition product vials made from the same CHHP/TCB solution, accurate changes in CHHP/TCB ratios could be calculated.

Examples 11–13 (Table II), and Examples 14–16 (Table III), give batch % t-butylhydroperoxide (t-BuOOH) and % cumenehydroperoxide (CumeneOOH) decomposition results, respectively for 1% Au/Carbon and 10% Au/SiO$_2$ catalysts. Analyses for t-BuOOH and CumeneOOH were done using a well known iodometric titration procedure, described in *Comprehensive Analytical Chemistry*, Elsevier Publishing Company, New York, Eds. C. L. Wilson, p. 756, 1960. Starting and product solutions of t-BuOOH and CumeneOOH in n-octane, followed by adding excess KI/acetic acid solution, were stirred in sealed vials at ambient temperature for 10 minutes and were titrated with 0.1 M Na$_2$S$_2$O$_3$ solution for amounts of I$_2$ liberated by the t-BuOOH and CumeneOOH present.

Examples 17–41 (Tables IV & V) were run as described for Examples 1–10 except that the reaction was run at 150° C. and chlorobenzene was used as a GC internal standard in place of TCB and undecane was used in place of n-octane solvent. In Tables IV and V, the amount of initial CHHP and final CHHP in the reaction was determined by calculating the area of the CHHP GC peak divided by the area of the chlorobenzene GC peak (area % CHHP/area % CB).

TABLE I

| EX. | Catalyst | Method of Prep | Approx. Wt % CHHP | Reaction Temp., ° C. | Time, min. | Wt % CHHP initial | Wt % CHHP final | % CHHP Decomp. |
|---|---|---|---|---|---|---|---|---|
| 1 | 1.4% Au/Carbon, 0.0100 | Exp. 1 | 2.2 | 125 | 10 | 0.407 | 0.221 | 45.7 |
| 2 | 1.4% Au/Carbon, 0.0103 | Exp. 1 | 2.2 | 125 | 10 | 0.537 | 0.281 | 47.7 |
| 3 | 1.4% Au/SiO$_2$, 0.0101 | Exp. 2 | 2.2 | 125 | 10 | 0.407 | 0.391 | 3.9 |
| 4 | 1.4% Au/SiO$_2$, 0.0101 | Exp. 2 | 2.2 | 125 | 10 | 0.537 | 0.430 | 19.9 |
| 5 | 14% Au/SiO$_2$, 0.0102 | Exp. 3 | 2.2 | 125 | 10 | 0.407 | 0.154 | 62.2 |
| 6 | 14% Au/SiO$_2$, 0.0104 | Exp. 3 | 2.2 | 125 | 10 | 0.407 | 0.131 | 67.8 |
| 7 | 0% Au/SiO$_2$, 0.0103 | Exp. 4 | 2.2 | 125 | 10 | 0.407 | 0.379 | 6.9 |
| 8 | 1.4% Au/Al$_2$O$_3$, 0.0102 | Exp. 5 | 2.2 | 125 | 10 | 0.537 | 0.449 | 16.4 |
| 9 | 13% Ag/SiO$_2$, 0.0102 | Exp. 6 | 2.2 | 125 | 10 | 0.407 | 0.245 | 39.8 |
| 10 | 4.5% Cu/SiO$_2$, 0.0103 | Exp. 7 | 2.2 | 125 | 10 | 0.407 | 0.119 | 70.8 |

TABLE II

| EX. | Catalyst, g | Method of prep. | Reaction Temp., ° C. | Time, min. | Wt % t-BuOOH initial | Wt % t-BuOOH final | % t-BuOOH Decomp. |
|---|---|---|---|---|---|---|---|
| 11 | 1.4% Au/Carbon, 0.0102 | Exp. 1 | 125 | 10 | 0.35 | 0.20 | 44 |
| 12 | 14% Au/SiO$_2$, 0.0102 | Exp. 3 | 125 | 10 | 0.35 | 0.18 | 48 |
| 13 | none | | 125 | 10 | 0.35 | 0.33 | 5 |

TABLE III

| EX. | Catalyst, g | Method of prep. | Reaction Temp., °C. | Time, min. | Wt % t-Cumene-(OOH) initial | Wt % t-Cumene-(OOH) final | % t-Cumene-(OOH) Decomp. |
|---|---|---|---|---|---|---|---|
| 14 | 1.4% Au/Carbon, 0.0103 | Exp. 1 | 125 | 10 | 0.55 | 0.32 | 42 |
| 15 | 14% Au/SiO$_2$, 0.0103 | Exp. 3 | 125 | 10 | 0.55 | 0.30 | 45 |
| 16 | none | | 125 | 10 | 0.55 | 0.54 | 2 |

TABLE IV

| EX. | Catalyst | Method of Prep | Approx. Wt % CHHP | Reaction Temp., °C. | Time, min. | CHHP/CB initial | CHHP/CB final | % CHHP Decomp. |
|---|---|---|---|---|---|---|---|---|
| 17 | 1% Au/MgO, 0.0102 | Exp. 8 | 2.2 | 150 | 5 | 3.41 | 3.29 | 3.5 |
| 18 | 1% Au/γ-Al$_2$O$_3$, 0.0120 | Exp. 9 | 2.2 | 150 | 5 | 3.41 | 0 | 100 |
| 19 | 1% Au/SiO$_2$, 0.0101 | Exp. 10 | 2.2 | 150 | 5 | 3.41 | 0.91 | 73.3 |
| 20 | 1% Au/TiO$_2$, 0.0106 | Exp. 11 | 2.2 | 150 | 5 | 3.41 | 2.26 | 33.6 |
| 21 | 1% Au/ZrO$_2$, 0.0054 | Exp. 12 | 2 | 150 | 0.5 | 5.26 | 4.68 | 11.1 |
| 22 | 1% Au, 0.1% Pd/Al$_2$O$_3$, 0.0051 | Exp. 13 | 2 | 150 | 0.5 | 4.82 | 3.01 | 37.5 |

TABLE V

| EX. | Catalyst, g. | Method of Prep | Approx. Wt % CHHP | Reaction Temp., °C. | Time, min. | CHHP/CB initial | CHHP/CB final | % CHHP Decomp. |
|---|---|---|---|---|---|---|---|---|
| 23 | CrZrO, 0.0099 | Exp. 14 | 2 | 150 | 5.0 | 5.94 | 0.44 | 92.6 |
| 24 | CrTaO, 0.0104 | Exp. 15 | 2 | 150 | 5.0 | 5.94 | 0.36 | 93.9 |
| 25 | CrTiO, 0.0109 | Exp. 16 | 2 | 150 | 5.0 | 4.55 | 0.00 | 100 |
| 26 | CoCrTiO, 0.0110 | Exp. 17 | 2 | 130 | 2.0 | 5.30 | 0.00 | 100 |
| 27 | TiSiO, 0.0054 | Exp. 18 | 2 | 150 | 0.5 | 4.59 | 4.05 | 11.8 |
| 28 | CoSiTiO, 0.0050 | Exp. 19 | 2 | 150 | 0.5 | 5.57 | 0.08 | 98.5 |
| 29 | AuMgCrTiO, 0.0055 | Exp. 20 | 2 | 150 | 0.5 | 4.64 | 4.32 | 7.0 |
| 30 | AuMgCrTiO, 0.0056 | Exp. 21 | 2 | 150 | 0.5 | 4.64 | 3.94 | 15.1 |
| 31 | AuMgCrZrO, 0.0054 | Exp. 22 | 2 | 150 | 0.5 | 5.18 | 3.96 | 23.6 |
| 32 | AuMgCrAlO, 0.0051 | Exp. 23 | 2 | 150 | 0.5 | 5.15 | 3.16 | 38.6 |
| 33 | AuMgCrAlO, 0.0053 | Exp. 24 | 2 | 150 | 0.5 | 5.15 | 2.62 | 49.2 |
| 34 | AuCrAlO, 0.0051 | Exp. 25 | 2 | 150 | 0.5 | 5.52 | 2.65 | 52 |
| 35 | CrAlO, 0.0054 | Exp. 26 | 2 | 150 | 0.5 | 5.52 | 5.24 | 6.9 |
| 36 | AuMgCoTiO, 0.0053 | Exp. 27 | 2 | 150 | 0.5 | 5.28 | 1.23 | 76.6 |
| 37 | CoCrZrO, 0.0052 | Exp. 28 | 2 | 150 | 0.5 | 5.26 | 0.54 | 88.7 |
| 38 | CrAlO, 0.0056 | Exp. 29 | 2 | 150 | 0.5 | 5.26 | 2.61 | 50.4 |
| 39 | CoNbTiO, 0.0054 | Exp. 30 | 2 | 150 | 0.5 | 5.57 | 3.30 | 40.8 |
| 40 | AuCrTiO, 0.0054 | Exp. 31 | 2 | 150 | 0.5 | 5.43 | 4.34 | 20 |
| 41 | AuAlO, 0.0053 | Exp. 32 | 2 | 150 | 0.5 | 5.52 | 4.86 | 11.9 |

TABLE VI

| EX. | Catalyst, g. | Method of Prep | Approx. Wt % CHHP | Reaction Temp., °C. | Time, min. | dK/dA | % CHHP Decomp. |
|---|---|---|---|---|---|---|---|
| 42 | AuCrAlO, 0.005 | Exp. 33 | 2 | 150 | 0.5 | 6.11 | 54.3 |
| 43 | NiCrAlO, 0.0053 | Exp. 34 | 2 | 150 | 0.5 | 4.9 | 22 |
| 44 | CoFeAlO, 0.0057 | Exp. 35 | 2 | 150 | 0.5 | 0.69 | 14 |
| 45 | NiCrTiO, 0.0051 | Exp. 36 | 2 | 130 | 0.5 | 5.98 | 23 |
| 46 | FeNiCoTiO, 0.0054 | Exp. 37 | 2 | 150 | 0.5 | 0.68 | 10.7 |

Examples 47–63 were run in a liquid full plug flow reactor, 30 inches (76 cm) with a ¼ inch (0.64 cm) diameter. Inlet and exit pressure was 150 psig (1.03 MPa gauge) controlled with a back pressure regulator. The catalysts were all prepared as in Experiment 13 on 2 mm spheres with the appropriate metal salts and type of alumina, with the exception that reduction was performed by flowing H$_2$ at 150° C. instead of sodium citrate. The feed consisted of 1.6% CHHP in cyclohexane, about 1% K and 2% A, and varying amounts of water and acid impurities consisting of monobasic and dibasic acids which would be typical of those produced in cyclohexane oxidation such as adipic acid, succinic acid, formic acid, and hydroxycaproic acid, in approximately equal amounts. Analyses were performed on CHHP, K, and A by gas chromatography. Cyclohexane, CHHP, K, and A were obtained from E. I. du Pont de Nemours and Company, Wilmington, Del. The K/A ratio obtained after conversion of cyclohexylhydroperoxide over the catalyst was calculated using the equation:

$$\frac{(\text{mols } K \text{ in product}) - (\text{mols } K \text{ in feed})}{(\text{mols } A \text{ in product}) - (\text{mols } A \text{ in feed})}$$

TABLE VII

| Ex. | Catalyst | % CHHP Conv. | K/A |
|---|---|---|---|
| 47 | 1%Au-0.1%Pd/γ-Al$_2$O$_3$ | 64 | 1.1 |
| 48 | 1%Au-0.1%Pt/γ-Al$_2$O$_3$ | 64 | 1.1 |
| 49 | 1%Au-0.1%Ru/γ-Al$_2$O$_3$ | 21 | 1.01 |
| 50 | 1%Au-0.1%Ni/γ-Al$_2$O$_3$ | 34 | 1.00 |
| 51 | 1%Au-0.1%Co/γ-Al$_2$O$_3$ | 45 | 1.02 |
| 52 | 1%Au-0.1%Pd/α-Al$_2$O$_3$ | 67 | 1.91 |
| 53 | 1%Au-0.1%Pt/α-Al$_2$O$_3$ | 68 | 1.84 |

TABLE VIII

| Ex. | Catalyst | Gas, sccm | % CHHP Conv. | K/A | Feed Benzene, ppm | Exit Benzene, ppm |
|---|---|---|---|---|---|---|
| 54 | 1%Au-0.1%Pd/α-Al$_2$O$_3$ | 0 | 60 | 1.63 | — | — |
| 55 | 1%Au-0.1%Pd/α-Al$_2$O$_3$ | N$_2$, 75 | 62 | 1.74 | — | — |
| 56 | 1%Au-0.1%Pd/α-Al$_2$O$_3$ | H$_2$, 75 | 78 | 0.47 | — | — |
| 57 | 1%Au-0.1%Pd/α-Al$_2$O$_3$ | H$_2$, 25 | 66 | 0.61 | — | — |
| 58 | 1%Au-0.1%Pd/α-Al$_2$O$_3$ | H$_2$, 10 | 61 | 0.73 | — | — |
| 59 | 1%Au-0.1%Pd/γ-Al$_2$O$_3$ | H$_2$, 75 | 51 | 0.31 | — | — |
| 60 | 1%Au-0.1%Pd/α-Al$_2$O$_3$ | H$_2$, 75 | — | — | 5140 | 4828 |
| 61 | 1%Au-0.1%Pd/α-Al$_2$O$_3$ | 0 | — | — | 5140 | 5140 |
| 62 | 1%Au-0.18%Pt/α-Al$_2$O$_3$ | 0 | 51 | 1.84 | — | — |
| 63 | 1%Au-0.18%Pd/α-Al$_2$O$_3$ | H$_2$, 75 | 73 | 0.41 | — | — |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

We claim:

1. An improved process for decomposing a hydroperoxide to form a decomposition reaction mixture containing a corresponding alcohol and ketone, the improvement comprising decomposing a hydroperoxide by contacting the hydroperoxide with a catalytic amount of a heterogeneous catalyst selected from the group consisting of elemental gold, silver, and copper, wherein 0 to 18% of one or more metals selected from Periodic Group VIII is/are also present with the heterogeneous catalyst.

2. The process according to claim 1 wherein the heterogeneous catalyst is supported on a catalyst support member.

3. The process according to claim 2 wherein the catalyst support member is selected from the group consisting of SiO$_2$, Al$_2$O$_3$, carbon, TiO$_2$, MgO, and zirconia.

4. The process according to claim 1 wherein the hydroperoxide is cyclohexylhydroperoxide.

5. The process according to claim 1 wherein the decomposition reaction temperature is from about 80° C. to about 170° C., and decomposition reaction pressure is from about 69 kPa to about 2760 kPa.

6. The process according to claim 5 wherein the reaction pressure is from about 276 kPa to about 1380 kPa.

7. The process according to claim 1 wherein the reaction mixture contains from about 0.5 to about 100 percent by weight cyclohexyl hydroperoxide.

8. The process according to claim 1 wherein the process is run in the presence of cyclohexane.

9. The process according to claim 1 wherein the process is run in the presence of added oxygen.

10. The process according to claim 2 wherein the heterogeneous catalyst is gold.

11. The process according to claim 10 wherein the gold is supported on zirconia or alumina.

12. The process according to claim 10 wherein the gold is from about 0.1 to about 10 wt. percent of the catalyst and support member.

13. The process according to claim 10 wherein the gold is present on the support member as well-dispersed particles having a diameter from about 3 nm to about 15 nm.

14. The process according to claim 1 wherein the Group VIII metal is Pd or Pt.

15. The process according to claim 1 wherein the process is run in the presence of hydrogen.

16. The process of claim 1 wherein the catalyst support member is alumina.

17. An improved process for decomposing a hydroperoxide to form a decomposition reaction mixture containing a corresponding alcohol and ketone, the improvement comprising decomposing a hydroperoxide by contacting the hydroperoxide with a catalytic amount of a heterogeneous catalyst, prepared by a sol-gel method, comprised of (a) one or more members selected from a first group consisting of Au, Cr, Co and Ti and (b) one or more members selected from a second group consisting of Fe, Ni, Zr, Ta, Nb, Al, Mg and Ti, wherein the selected members of (b) are combined with an oxide and wherein members of the first group cannot be the same as members of the second group.

18. The process according to claim 17 wherein the heterogeneous catalyst contains Cr and/or Co.

19. The process according to claim 18 wherein the heterogeneous catalyst comprises Au and Cr.

20. The process according to claim 17 wherein the oxide is an inorganic matrix of hydroxides or oxides, or combinations thereof.

21. The process according to claim 17 wherein the hydroperoxide is cyclohexylhydroperoxide.

22. The process according to claim 17 wherein the process is run in the presence of added oxygen.

* * * * *